United States Patent [19]

Bergougnan et al.

[11] Patent Number: 5,569,793
[45] Date of Patent: Oct. 29, 1996

[54] PROCESS FOR THE PRODUCTION OF 1,1,1-CHLORODIFLUOROETHANE

[75] Inventors: Michel Bergougnan, Pierre-Benite; Jean-Michel Galland; Sylvain Perdrieux, both of Vernaison, all of France

[73] Assignee: Societe Atochem, Paris, France

[21] Appl. No.: 480,703

[22] Filed: Jun. 7, 1995

Related U.S. Application Data

[63] Continuation of Ser. No. 181,480, Jan. 14, 1994, abandoned, which is a continuation of Ser. No. 876,691, Apr. 28, 1992, abandoned, which is a continuation of Ser. No. 592,387, Oct. 3, 1990, abandoned.

[30] Foreign Application Priority Data

Oct. 3, 1989 [FR] France ................... 89 12918

[51] Int. Cl.$^6$ ................... C07C 17/08
[52] U.S. Cl. ................... 570/167; 570/168; 570/169
[58] Field of Search ................... 570/167, 168, 570/169

[56] References Cited

U.S. PATENT DOCUMENTS 4,091,043  5/1978  Ohsaka et al. .
4,849,555  7/1989  Cheminal et al. .

FOREIGN PATENT DOCUMENTS 2659046  7/1977  Germany ................... 570/167
1150919  5/1986  U.S.S.R. ................... 570/167

OTHER PUBLICATIONS

J. Soc. Chem Ind vol. 66 pp. 427–429 (1947) Whalley.
Chemicals Abstract, vol. 82, 1975, p. 468, No. 111560v.
Chemical Abstracts, vol. 85, 1976, p. 593, No. 123323v.

*Primary Examiner*—Alan Siegel
*Attorney, Agent, or Firm*—Spencer & Frank

[57] ABSTRACT

The invention relates to continuous production of 1,1,1-chlorodifluoroethane from 1,1,1-trichloroethane and hydrofluoric acid by reaction in liquid phase in the presence of at least one fluorination catalyst. According to the invention, the process is carried out under an absolute pressure of between 6 and 30 bars and at a temperature of between 50° and 120° C., the content of catalyst(s) in the reaction mixture, expressed as a percentage by weight of metal, being between 0.05 and 10% and the content of organohalogenated by-products not belonging to series 140 in the reaction mixture being controlled at a value below 40% by weight. This process makes it possible, at the same time, to obtain a high degree of conversion of hydrofluoric acid, to minimize the coproduction of 1,1,1-trifluoroethane and organohalogenated by-products and to facilitate the recovery of the hydrochloric acid formed.

10 Claims, No Drawings

PROCESS FOR THE PRODUCTION OF 1,1,1-CHLORODIFLUOROETHANE

This is a continuation of application Ser. No. 08/181,480, filed on Jan. 14, 1994 now abandoned; which is a continuation application of Ser. No. 07/876,691 filed on Apr. 28, 1992 (abandoned); which is a continuation applicaton of Ser. No. 07/592,387 filed on Oct. 3, 1990 (abandoned).

FIELD OF THE INVENTION

The present invention relates to a process for the continuous and selective production of 1,1,1-chlorodifluoroethane by fluorination of 1,1,1-trichloroethane with anhydrous hydrofluoric acid in liquid phase and in the presence of a catalyst.

BACKGROUND OF THE INVENTION 1,1,1-chlorodifluoroethane (designated 142b below) is used as a starting material for the production of vinylidene fluoride, as a propellant in the aerosol industry, as a swelling agent in the foam industry and as a cooling liquid.

The production of 142b from 1,1,1-trichloroethane (designated T111 below) and hydrofluoric acid (HF) in particular by the processes termed "liquid phase", with or without catalyst, has been known for a long time.

The reaction proceeds in the following simplified manner:

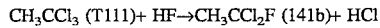

$CH_3CCl_3$ (T111)+ HF→$CH_3CCl_2F$ (141b)+ HCl

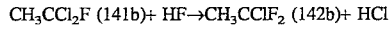

$CH_3CCl_2F$ (141b)+ HF→$CH_3CClF_2$ (142b)+ HCl

However, side reactions are produced which are undesirable from the standpoint of a selective production of 142b. By way of example, the fluorination can continue to 1,1,1-trifluoroethane (143a):

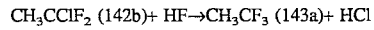

$CH_3CClF_2$ (142b)+ HF→$CH_3CF_3$ (143a)+ HCl

Other parasitic reactions can result depending on the reaction conditions, such as dehydrochlorinations, dimerizations, etc., followed by fluorinations or chlorinations. These parasitic reactions lead to organohalogenated by-products which do not belong to the series termed "series 140" (T111, 141b, 142b, 143a).

A first objective of an industrial process for the production of 142b is to minimize the production of the undesirable by-products: 143a and products not belonging to series 140.

A second objective of an industrial process for the production of 142b is to maximize the conversion of hydrofluoric acid at the reaction level. Whatever the reaction system used, some of the hydrofluoric acid used is not consumed and this hydrofluoric acid must be recovered. This recovery is facilitated if the degree of conversion of hydrofluoric acid is high in the reaction system. It is known (see following discussion) that the production of 142b from T111 can be carried out in liquid phase without catalyst. However, in this case the degree of conversion of hydrofluoric acid in the reaction system is usually limited and the recovery of the unconverted hydrofluoric acid necessitates the use of expensive techniques downstream of the reaction. Because of this fact, catalysts have been sought which enable this reaction to be carried out with a high degree of conversion of hydrofluoric acid and in parallel with greater productivities.

A third objective of an industrial process for the production of 142b from T111 is to obtain economically a commercial grade of hydrochloric acid by-product, thus enabling its valorization. It is well known that one of the effective means for achieving this objective is to obtain anhydrous and purified hydrochloric acid by distillation downstream of the reaction system. However, this distillation of hydrochloric acid by-product necessitates, if it is to be economic, the use of an absolute pressure about 6 to 30 bars, more precisely about 10 to 20 bars. The use of such a pressure at the level of the distillation of anhydrous hydrochloric acid implies, for an industrial process, the fact of conducting the fluorination reaction under a pressure of at least the same order, such that gaseous reaction products (HCl and others) pass directly from the reaction system to the distillation.

Unfortunately, these diverse objectives, for an industrial process for the production of 142b from T111, appear contradictory to those skilled in the art. In fact, as the review of existing processes below show, the use of an active catalyst (enabling a high degree of conversion of hydrofluoric acid to be obtained) usually leads to an increased fluorination of the 140 series and thus to the production of a large fraction of undesirable 143a as a by-product, on the one hand, and to a likewise high proportion of by-products not belonging to series 140, on the other hand. Similarly, when the reaction conditions are chosen to minimize the proportion of 143a, the reaction mixture inevitably contains high proportions of T111 and 141b because the reactions concerned are consecutive. Now, these slightly fluorinated or unfluorinated molecules are the most unstable and, consequently, larger amounts of by-products not belonging to series 140 form a priori. Similarly, the fact of choosing a relatively high pressure to conduct the fluorination reaction (with a view to an economic recovery of hydrochloric acid) inevitably promotes, as is well known in fluorination, the production of more highly fluorinated compounds and thus a high proportion of 143a.

None of the processes for the fluorination of T111 known to date enables the three above mentioned objectives to be achieved simultaneously.

French Patent No. 798,421 describes succinctly the possibility of producing 141b, 142b and 143a from T111 and hydrofluoric acid at 150° C. without catalyst or in the presence of $SbF_3$. This patent gives no indication of the means for selectively obtaining 142b.

In the article J. Am. Chem. Soc. 58, 889–890 (1936), HENNE and RENOLL describe the possibility of producing 141b, 142b and 143a from T111 and hydrofluoric acid in the presence of $SbF_3$ and $SbF_3Cl_2$. However, this article does not mention the operating conditions enabling the production of 143a to be restricted.

In the article J. Soc. Chem. Ind. (London), 67, 331–333 (1948) BROWN and WHALLEY describe the possibility of producing 141b, 142b and 143a from T111 and hydrofluoric acid without catalyst, at 144° C. However, this article likewise does not mention the operating conditions enabling the production of 143a to be restricted.

The Japanese patent publication No. JP 74/3965 describes a process for obtaining 142b selectively from T111 and hydrofluoric acid in the presence of $SbCl_5$ catalyst, characterized in the main in that:

a) the reaction pressure is between 0 and 3 kg/cm² effective, b) the reaction is carried out in a series of two reactors, the first essentially forming 142b from 141b with an excess of hydrofluoric acid and the second forming essentially 141b from T111.

This reaction system concept makes it possible effectively to obtain a high overall degree of conversion of hydrofluoric acid and apparently a relatively low proportion of 143a (about 1.5% of the 142b formed).

However, this process is carried out under low pressure; it is certainly mentioned in this patent that if the reaction was conducted above an effective pressure of 3 kg/cm², the proportion of 143a would be considerably increased and that judicious choice of the reaction temperature would not make it possible to compensate for this effect. This process therefore does not permit optimum recovery of the hydrochloric acid by-product. Moreover, the process used to obtain a high degree of conversion of hydrofluoric acid is complex because it requires two reaction systems in series. Finally, this patent does not mention the proportion of by-products not belonging to series 140 formed.

U.S. Pat. No. 3,833,676 describes a process for the production of 142b from T111 and hydrofluoric acid in the absence of catalyst, characterized in the main in that the reaction is conducted in the presence of excess of hydrofluoric acid. It is obvious that, in this case, the degree of conversion of hydrofluoric acid in the reaction system is limited.

Japanese patent publication No. JP 76/29404 describes a process for the production of 142b from T111 and hydrofluoric acid in the presence of $MoCl_5$ catalyst. The selectivity problems posed by this reaction are explained in the text of this patent. If catalyst is not used, the degree of conversion of hydrofluoric acid is limited; if an active catalyst such as $SbCl_5$ is used, significant amounts of 143a are formed, in particular under pressure, or the reaction is limited to a lower proportion of 142b and simultaneously the degree of conversion of hydrofluoric acid decreases. This patent recommends the use of the catalyst $MoCl_5$ as being more selective than $SbCl_5$; however, no recommendation is found in this patent of precise operating conditions or of an example enabling a reaction using $MoCl_5$ or even $SbCl_5$ as catalyst to be conducted continuously and enabling less than 1% of 143a and a degree of conversion of hydrofluoric acid of more than 90% to be achieved simultaneously.

Japanese patent publication No. JP 76/39606 describes the use of metal oxides such as $MoO_3$ as fluorination catalyst in liquid phase. The example of the fluorination of T111 is mentioned. As in the above patent, precise operating conditions enabling a low proportion of 143a and a high degree of conversion of hydrofluoric acid to be obtained simultaneously are not described.

French Patent No. FR 2,337,120 describes a process for the production of 142b and/or 143a from T111 and hydrofluoric acid in the presence of $SbCl_5$ catalyst. The process is characterized in the main in that the reaction is conducted in a heavy and inert solvent. This patent teaches two examples where a low proportion of 143a and a high degree of conversion of hydrofluoric acid are noted at the same time (Examples 17 and 22). However, it is found that the recommended reaction pressures are low (from 0 to 5 kg/cm² effective) and that the two examples mentioned above are conducted at 0 and 1 kg/cm². It is obvious that if the reaction pressures were higher the proportions of 143a would also be higher. Moreover, the recommended reaction temperatures are low, from 10° to 65° C., in relation with the low pressures, and the patent teaches that higher reaction temperatures lead to the formation of undesirable by-products. The use of a heavy solvent therefore enables variable proportions of 143a to be obtained, but in no case enables the formation of the latter to be minimized, in particular under a pressure higher than 5 kg/cm² effective.

In a continuous process fluorination of T111 in liquid phase, the liquid reaction mixture necessarily contains a proportion of organohalogenated products not belonging to series 140, which originate from impurities in the starting material or are formed, by side reactions, from compounds of series 140 which are present. Some of these products have relatively high boiling points. Without any particular precaution, the content of these products in the reaction mixture can therefore be high.

It has now been found that a direct relationship exists between the content of these organohalogenated products in the reaction mixture and the production of 143a as a by-product, this latter production being higher, the higher the content of by-products not belonging to series 140 in the reaction mixture, and that it is therefore necessary to regulate the content of products not belonging to series 140 in the reaction mixture to less than 40% by weight, and preferably less than 10% by weight, to minimize the production of 143a as a by-product.

Correlatively, the contents of compounds of series 140 in the reaction mixture are high, in particular those of T111 and of 141b. Although the production of undesirable by-products from these elements is facilitated a priori, it has also been found that under certain conditions this was curiously not the case.

In other words, subject to regulating the pressure, the temperature, the active catalyst content and the content of by-products not belonging to series 140 in the ranges indicated below, it is possible to achieve the three above mentioned objectives simultaneously.

DETAILED DESCRIPTION OF THE INVENTION

The process according to the present invention for the continuous production of 1,1,1-chlorodifluoroethane from 1,1,1-trichloroethane and hydrofluoric acid by reaction in liquid phase in the presence of at last one fluorination catalyst is characterized by the combination of the following measures:

a) the absolute pressure of the reaction system is chosen between 6 and 30 bars, preferably between 10 and 20 bars;

b) the total content of catalyst(s) in the liquid reaction mixture, expressed as a percentage by weight of metal, is between 0.05 and 10%, preferably between 0.1 and 5%;

c) the reaction temperature is chosen between 50° and 120° C., preferably between 70° and 100° C.; and d) the content of by-products not belonging to series 140 in the liquid reaction mixture is controlled to remain below 40% by weight and preferably below 10% by weight.

Operating under these conditions it has been found that:

the proportion of 143a by-product was very low, typically equal to or below about 1% by weight of the production of 142b the rate of production of by-products not belonging to series 140 was very low, typically equal to or below about 1.5% by weight of the production of 142b, and the degree of conversion of hydrofluoric acid at the outlet from the reaction system was high, typically greater than 90%, and that these results were achieved despite a high reaction pressure, enabling a purification by distillation of the hydrochloric acid by-product in anhydrous form.

The fluorination catalyst or catalysts used in the process according the invention are well-known active catalysts such as the halides, oxides and oxyhalides of the elements of groups IVa and b, Va and b, VIa and b and VIII. A typical example is antimony pentachloride or more precisely the chlorofluorides of pentavalent antimony which are formed in situ by partial fluorination of $SbCl_5$. If necessary, the activity of the catalysts can be maintained by known means such as, for example, an injection of chlorine in the case of antimony chlorides.

The content of by-products not belonging to series 140 in the liquid reaction mixture can be adjusted by the removal of the reaction products from the reaction system in two forms: a removal in gaseous form and removal in liquid form.

The process according to the invention can be carried out in conventional equipment known to those skilled in the art. It can consist of a single reactor fed, in gaseous or liquid form, with the starting materials (T111 and HF) and the recycled products and adequately heated or cooled. It must promote the contact between the reactants by an appropriate geometry, an appropriate means of introduction of the reactants and an appropriate mixing technique. This reactor can be surmounted by a reflux column and a reflux condenser enabling avoiding entrainment of the catalyst or catalysts in the gaseous flow issuing from the reactor and adjusting the composition for organofluorinated compounds in this flow (content of 142b, 141b, T111, etc. . . .).

The starting materials or recycled products (T111, 141b, HF) are fed to the reactor in the ratio adequate for a production 142b. For complete recycling of the unconverted products (HF, T111, 141b), this signifies a molar ratio of fresh HF/fresh T111 close to stoichiometry, that is to say about 2.

As indicated above, the reaction equipment can comprise a liquid outlet for reaction products. This outlet in liquid form is one of the possible means enabling adjustment of the content of products not belonging to series 140 in the reaction mixture.

The gaseous and, where appropriate, liquid flows issuing from the reaction are treated in the conventional manner to separate the useful final products (142b, HCl). Regarding recovery of hydrochloric acid, this treatment comprises, in particular, a distillation of anhydrous HCl. The unconverted T111 and 141b, the small amount of unconverted hydrofluoric acid and the catalyst or catalysts used contained in the liquid issuing from the reactor are recycled to the reaction system.

EXAMPLES

The following Examples 1 and 2 illustrate the invention without restricting it. Examples 3 and 4 are given by way of comparison to demonstrate the value of the operating parameters specified according to the invention.

Example 1

A conventional 5 m³ fluorination reactor made of ordinary steel and surmounted by a reflux column and a reflux condenser is used. This reactor is provided with continuous feeds of fresh and recycled T111, recycled 141b, fresh and recycled HF, chlorine and antimony pentachloride.

The reaction pressure is controlled at 11 bars absolute. The temperature of the reaction mixture is controlled at 79° C. by heating the reactor through a double wall.

The addition of antimony pentachloride is controlled to obtain an antimony content (calculated as Sb metal) of 1% by weight in the reaction mixture.

A withdrawal in gaseous form is effected downstream of the reflux condenser located at the top of the column surmounting the reactor. A withdrawal in liquid form is carried out from the reactor itself and controlled to obtain 4.3% by weight of by-products not belonging to series 140 in the reaction mixture.

These two withdrawals are directed towards conventional treatment devices for the recovery or recycling of the products.

The material balance, indicated in Table 1 which follows, shows the value of these operating conditions. The following simultaneous performances can be established:

a) operating pressure 11 bars absolute,
b) degree of conversion of hydrofluoric acid 90.5% c) proportion of 143a formed relative to the production of 142b
$$\frac{143a}{142b} = \frac{6.1}{915.5} = 0.5\% \text{ by weight}$$

d) proportion of by-products (BP) not belonging to series 140 formed relative to the production of 142b
$$\frac{BP}{142b} = \frac{12.9}{915.5} = 1.4\% \text{ by weight}$$

TABLE 1

MATERIAL BALANCE kg/h

| Products | Feed or Recycling | Gas Withdrawal (condenser outlet) | Liquid withdrawal (reactor outlet) |
|---|---|---|---|
| HCl | — | 676.4 | ε |
| HF | 407.9 (fresh + recycled) | 38.6 | ε |
| 143a | — | 6.1 | ε |
| 142b | — | 860 | 55.5 |
| 141b | 234.6 (recycled) | 35.1 | 199.5 |
| T111 | 1267.9 (fresh + recycled) | ε | 32.1 |
| Cl₂ | 5.8 | ε | ε |
| Sb (1) | 3 (recycled) | — | 3 |
| BP (2) | — | — | 12.9 |

(1) Expressed as antimony metal
(2) Organohalogenated by-products not belonging to series 140

Example 2

The same reactor is used as in Example 1.

The reaction pressure is controlled at 16 bars absolute. The temperature of the reaction mixture is controlled at 75° C.

The addition of antimony pentachloride is controlled to obtain an antimony content in the reaction mixture (calculated as Sb metal) of 1.1% by weight.

The liquid withdrawal from the reactor is controlled to obtain 3% by weight of by-products not belonging to series 140 in the reaction mixture.

The material balance, indicated in Table 2, enables the following simultaneous performances to be established:

| | |
|---|---|
| a) operating pressure | 16 bars absolute, |
| b) degree of conversion of hydrofluoric acid | 91.2% |
| c) proportion of 143a formed relative to the production of 142b | $\dfrac{143a}{142b} = \dfrac{4.6}{480} = 1\%$ by weight |
| d) proportion of by-products not belonging to series 140 formed relative to the production of 142b | $\dfrac{BP}{142b} = \dfrac{5.9}{480} = 1.2\%$ by weight |

TABLE 2

MATERIAL BALANCE kg/h

| Products | Feed or Recycling | Gas withdrawal (condenser outlet) | Liquid withdrawal (reactor outlet) |
|---|---|---|---|
| HCl | — | 356 | ε |
| HF | 213.3 (fresh + recycled) | 18.8 | ε |
| 143a | — | 4.6 | ε |
| 142b | — | 421.4 | 58.6 |
| 141b | 167.3 (recycled) | 86.3 | 81.0 |
| T111 | 688.9 (fresh + recycled) | ε | 39.5 |
| Cl₂ | 2.6 | ε | ε |
| Sb (1) | 2.1 (recycled) | — | 2.1 |
| BP (2) | — | — | 5.9 |

(1) Expressed as antimony metal
(2) Organohalogenated by-products not belonging to series 140

Comparative Example 3

The same reactor is used as in Example 1. The pressure is controlled at 11 bars absolute and the temperature of the reaction mixture at 75° C.

The addition of antimony pentachloride is controlled to obtain an antimony content (calculated as Sb metal) of 1.3% by weight in the reaction mixture and the liquid withdrawal from the reactor is controlled to obtain 52% by weight of by-products not belonging to series 140 in the reaction mixture (that is a value higher than the threshold recommended according to the invention).

The material balance for such an operation is indicated in Table 3. The following performances are obtained:

| | |
|---|---|
| a) operating pressure | 11 bars absolute, |
| b) degree of conversion of hydrofluoric acid | 90.4% |
| c) proportion of 143a formed relative to the production of 142b | $\dfrac{143a}{142b} = \dfrac{19.9}{410.5} = 4.9\%$ by weight |
| d) proportion of by-products not belonging to series 140 formed relative to the production of 142b | $\dfrac{BP}{142b} = \dfrac{5.3}{410.5} = 1.3\%$ by weight |

By comparison with Examples 1 and 2, it is found that the proportion of undesirable 143a formed is about 5 times higher.

TABLE 3

MATERIAL BALANCE kg/h

| Products | Feed or Recycling | Gas withdrawal (condenser outlet) | Liquid withdrawal (reactor outlet) |
|---|---|---|---|
| HCl | — | 325.7 | ε |
| HF | 196.7 (fresh + recycled) | 18.8 | ε |
| 143a | — | 19.9 | ε |
| 142b | — | 407.7 | 2.8 |
| 141b | 7.6 (recycled) | 5.4 | 2.2 |
| T111 | 581.5 (fresh + recycled) | ε | 0.7 |
| Cl₂ | 2.7 | ε | ε |
| Sb (1) | 0.14 (recycled) | — | 0.14 |
| BP (2) | — | — | 5.3 |

(1) Expressed as antimony metal
(2) Organohalogenated by-products not belonging to series 140

Comparative Example 4

In this example a run is carried out at low pressure, below the threshold recommended according to the invention. A reaction temperature and catalyst content close to those of Examples 1 and 2 are maintained. Under these conditions, to obtain a stable operation, it proves impossible to significantly lower the content of by-products not belonging to series 140 in the reaction mixture and this content is therefore necessarily higher than the recommended threshold.

The same reactor is used as in Example 1. The pressure is controlled at 4.5 bars absolute and the temperature of the reaction mixture is controlled at 75° C.

The addition of antimony pentachloride is adjusted so as to obtain an antimony content in the reaction mixture (calculated as Sb metal) of 1.3% by weight.

The liquid withdrawal from the reactor is controlled so as to obtain 93% by weight of by-products not belonging to series 140 in the reaction mixture.

The material balance, indicated in Table 4, enables the following performances to be established for such an operation:

| | |
|---|---|
| a) operating pressure | 4.5 bars absolute, |
| b) degree of conversion of hydrofluoric acid | 92.5% |
| c) proportion of 143a formed relative to the production of 142b | $\dfrac{143a}{142b} = \dfrac{38.6}{375.3} = 10.3\%$ by weight |
| d) proportion of by-products not belonging to series 140 formed relative to the production of 142b | $\dfrac{BP}{142b} = \dfrac{9.3}{375.3} = 2.5\%$ by weight |

It is found that this mode of operation at a pressure not permitting easy recovery of the hydrochloric acid formed also leads to proportions of 143a and of by-products not belonging to series 140 which are very much higher than those observed in Examples 1 and 2 according to the invention.

TABLE 4

| | MATERIAL BALANCE kg/h | | |
|---|---|---|---|
| Products | Feed | Gas withdrawal | Liquid withdrawal |
| HCl | — | 326.9 | ε |
| HF | 192.4 (fresh + recycled) | 14.6 | ε |
| 143a | — | 38.6 | ε |
| 142b | — | 375.1 | 0.2 |
| 141b | 15.5 (recycled) | 15.3 | 0.2 |
| T111 | 567.7 (fresh + recycled) | ε | 0.3 |
| $Cl_2$ | 4.9 | ε | ε |
| Sb (1) | 0.13 (recycled) | — | 0.13 |
| BP (2) | — | — | 9.3 |

(1) Expressed as antimony metal
(2) Organohalogenated by-products not belonging to series 140

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the continuous production of 1,1,1-chlorodifluoroethane from 1,1,1-trichloroethane and hydrofluoric acid by reaction in liquid phase in the presence of at least one fluorination catalyst, comprising, conducting the reaction under an absolute pressure of between 10 and 30 bars, with a content of catalyst, expressed as a percentage by weight of metal in the liquid reaction mixture, of between 0.05 and 10% at a temperature of between 50° and 120° C., and with the content of organohalogenated compounds in the liquid reaction mixture other than 1,1,1-trichloroethane, 1,1,1-dichlorofluoroethane, 1,1,1-chlorodifluoroethane and 1,1,1-trifluoroethane being controlled at less than 40% by weight by relative adjustment of the removals in gaseous and liquid form of the reaction products from the reaction system.

2. Process according to claim 1, wherein the reaction is conducted under an absolute pressure of between 10 and 20 bars.

3. Process according to claim 1, wherein the fluorination catalyst or catalysts are chosen from the halides, oxides and/or oxyhalides of elements of groups IVa and b, Va and b, VIa and b and VIII.

4. Process according to claim 3, wherein the reaction is conducted in the presence of antimony chlorofluorides as catalyst.

5. Process according to claim 1, wherein the content of catalyst in the reaction mixture is between 0.1 and 5% by weight of metal.

6. Process according to claim 1, wherein the reaction temperature is between 70° and 100° C.

7. Process according to claim 1, wherein the content of the organohalogenated by-products in the liquid reaction mixture is controlled at less than 10% by weight.

8. Process for the continuous production of 1,1,1-chlorodifluoroethane from 1,1,1-trichloroethane and hydrofluoric acid by reaction in liquid phase in the presence of at least one fluorination catalyst, consisting essentially of, (a) conducting the reaction under absolute pressure of between 10 and 30 bars, (b) with a content of catalyst, expressed as a percentage by weight of metal in the liquid reaction mixture, of between 0.05 and 10%, (c) at a temperature of between 50° and 120° C., (d) with the content of organohalogenated compounds in the liquid reaction mixture other than 1,1,1-trichloroethane, 1,1,1-dichlorofluoroethane, 1,1,1-chlorodifluoroethane and 1,1,1-trifluoroethane being controlled at less than 40% by weight by relative adjustment of the removals in gaseous and liquid form of the reaction products from the reaction system, and (f) recovering anhydrous hydrochloric acid from the removed reaction products.

9. The process of claim 8 wherein the temperature is between about 70° and 120° C.

10. The process of claim 8 wherein step (f) comprises recovering anhydrous hydrochloric acid by a distillation step.

* * * * *